(12) United States Patent
Calandra et al.

(10) Patent No.: US 11,155,518 B2
(45) Date of Patent: Oct. 26, 2021

(54) PEROXYHEMIACETAL PROFRAGRANT AND PROFLAVOR COMPOUNDS

(71) Applicant: Firmenich SA, Geneva (CH)

(72) Inventors: Michael J. Calandra, Plainsboro, NJ (US); Ying Wang, Plainsboro, NJ (US); John Impellizzeri, Plainsboro, NJ (US)

(73) Assignee: Firmenich SA, Satigny (CH)

( * ) Notice: Subject to any disclaimer, the term of this patent is extended or adjusted under 35 U.S.C. 154(b) by 564 days.

(21) Appl. No.: 15/768,031

(22) PCT Filed: Oct. 19, 2016

(86) PCT No.: PCT/EP2016/075078
§ 371 (c)(1),
(2) Date: Apr. 13, 2018

(87) PCT Pub. No.: WO2017/067975
PCT Pub. Date: Apr. 27, 2017

(65) Prior Publication Data
US 2018/0319745 A1    Nov. 8, 2018

Related U.S. Application Data

(60) Provisional application No. 62/243,609, filed on Oct. 19, 2015.

(51) Int. Cl.
| | |
|---|---|
| *C07C 409/20* | (2006.01) |
| *A23L 2/56* | (2006.01) |
| *C11D 3/50* | (2006.01) |
| *A23L 27/20* | (2016.01) |
| *A23G 3/36* | (2006.01) |
| *A23L 2/39* | (2006.01) |
| *C11B 9/00* | (2006.01) |

(52) U.S. Cl.
CPC .............. *C07C 409/20* (2013.01); *A23G 3/36* (2013.01); *A23L 2/39* (2013.01); *A23L 2/56* (2013.01); *A23L 27/203* (2016.08); *A23L 27/2026* (2016.08); *A23L 27/2028* (2016.08); *C11B 9/0015* (2013.01); *C11B 9/0034* (2013.01); *C11D 3/507* (2013.01); *C07C 2601/16* (2017.05)

(58) Field of Classification Search
CPC .............. C07C 409/20; C07C 2601/16; A23L 27/2026; A23L 27/2028; A23L 2/39; A23L 2/56; A23L 27/203; A23G 3/36; C11B 9/0015; C11B 9/0034; C11D 3/507
See application file for complete search history.

(56) References Cited

U.S. PATENT DOCUMENTS

| 6,096,704 A | 8/2000 | Bryant, Jr. et al. |
| 2006/0029705 A1* | 2/2006 | McPherson .............. A23L 27/70 |
| | | 426/534 |

OTHER PUBLICATIONS

International Search Report and Written Opinion for international application No. PCT/EP2016/075078 dated Dec. 23, 2016.
Calandra et al., "Terpene hydroperoxide chemistry in citrus oils; reaction with endogenous aldehydes to form peroxyhemiacetals", Flavour Fragr. J., 2016, vol. 31, pp. 241-249.

* cited by examiner

*Primary Examiner* — Nikki H. Dees
(74) *Attorney, Agent, or Firm* — Armstrong Teasdale LLP

(57) ABSTRACT

Provided herein is a compound of Formula I:

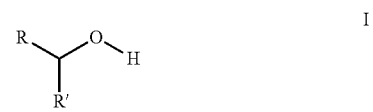

wherein R represents a terpene hydroperoxyl selected from the group consisting of

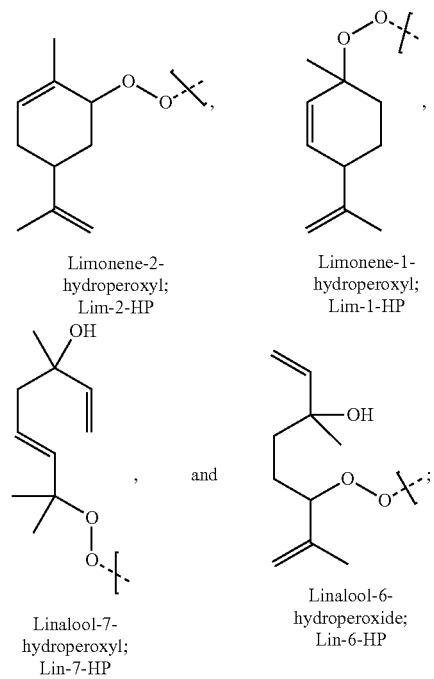

Limonene-2-hydroperoxyl; Lim-2-HP Limonene-1-hydroperoxyl; Lim-1-HP Linalool-7-hydroperoxyl; Lin-7-HP Linalool-6-hydroperoxide; Lin-6-HP wherein R' represents a alkyl group selected from the group consisting: $CH_3(CH_2)_8-$, $CH_3(CH_2)_6-$, and $CH_3-$.

5 Claims, 2 Drawing Sheets

PEROXYHEMIACETAL PROFRAGRANT AND PROFLAVOR COMPOUNDS

RELATED APPLICATIONS

This application is a national stage application under 35 U.S.C. § 371 filing of International Patent Application PCT/EP2016/075078, filed Oct. 19, 2016, which claims the benefit of US Provisional Application n° 62/243,609 filed 19 Oct. 2015.

FIELD

The present invention relates to the field of perfumery and flavors. More particularly, it concerns the use of peroxyhemiacetals as precursors for the release of a flavor or a fragrance in the form of an aldehyde.

BACKGROUND

The flavors and fragrance industry has a particular interest in compounds which are capable of being released over time and that can deliver beneficial effects such as an odoriferous effect or an enhanced flavor. Various means to control the release of flavors and fragrances from precursor compounds have been reported. It is desirable for the F&F industry to have a precursor that may release flavors and fragrances in response to various stimuli such as, but not limited to, light, water, air, heat, pH, and oxidation.

SUMMARY

Provided herein is a compound of Formula I:

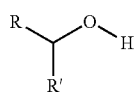

I wherein R represents a terpene hydroperoxyl selected from the group consisting of

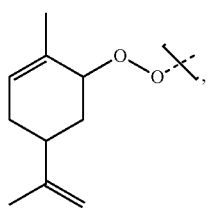

Limonene-2-
hydroperoxyl;
Lim-2-HP

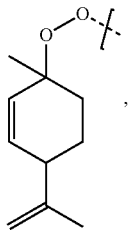

Limonene-1-
hydroperoxyl;
Lim-1-HP

-continued

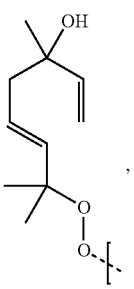

Linalool-7-
hydroperoxyl;
Lin-7-HP and

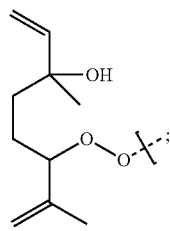

Linalool-6-
hydroperoxide;
Lin-6-HP wherein R' represents an alkyl group selected from the group consisting of: $CH_3(CH_2)_8-$, $CH_3(CH_2)_6-$, and $CH_3-$.

Further provided herein is a method of delivering a compound selected from the group consisting of decanal, octanal and acetaldehyde comprising adding to an aqueous solution a compound of Formula I as defined in claim 1.

Also provided herein is a use of a compound of Formula I comprising adding a compound of Formula I to an aqueous solution.

Still yet further provided is a method to improve, enhance or modify odoriferous properties of a perfuming composition or a perfumed article, which method comprises adding to said composition or article an effective amount of a compound of Formula I.

Still further provided is a method to improve, enhance or modify taste or aromatic properties of a flavoring composition or a flavored article, which method comprises adding to said composition or article an effective amount of a compound of Formula I.

DETAILED DESCRIPTION

Figure 1:
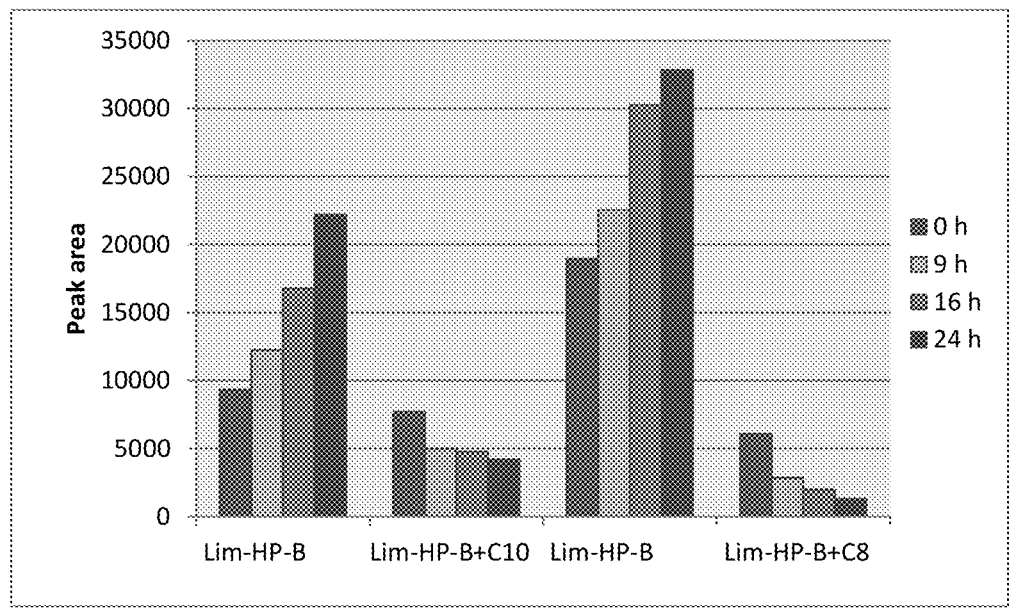
FIG. 1 shows the appearance of the limonene hydroperoxides that accompanies the appearance of the aldehyde moiety along with the loss of the peroxyhemiacetal.

Provided herein are the peroxyhemiacetal compounds listed below. The compounds can be made according to the procedure set forth as set below under preparation and methods.

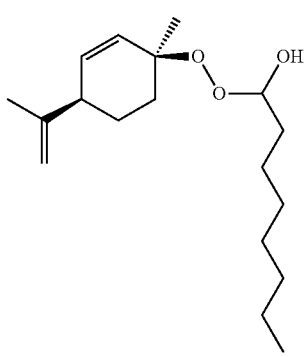

Peroxyhemiacetal made from
Lim-1-HP & Octanal

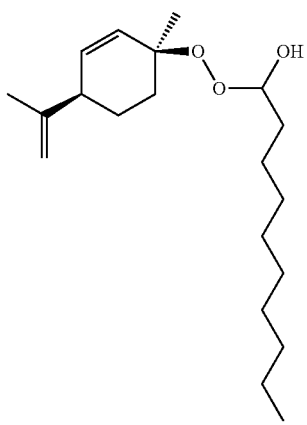

Peroxyhemiacetal made from
Lim-1-HP & Decanal

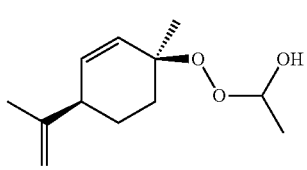

Peroxyhemiacetal made from
Lim-1-HP & Acetaldehyde

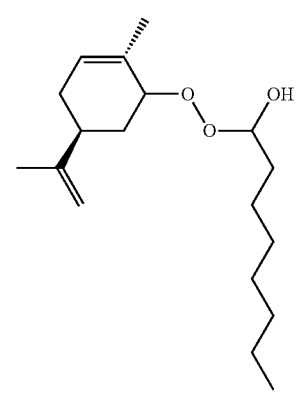

Peroxyhemiacetal made from
Lim-2-HP & Octanal

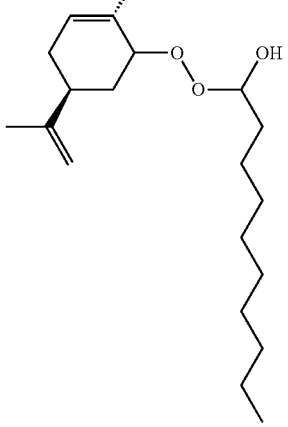

Peroxyhemiacetal made from
Lim-2-HP & Decanal

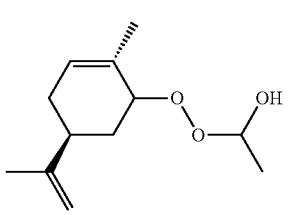

Peroxyhemiacetal made from
Lim-2-HP & Acetaldehyde

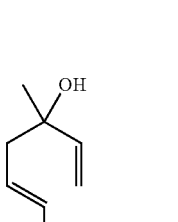 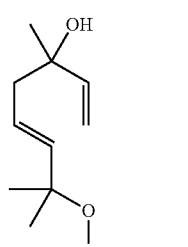

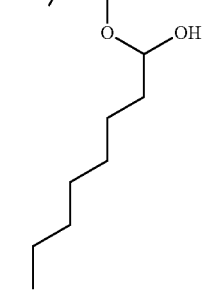 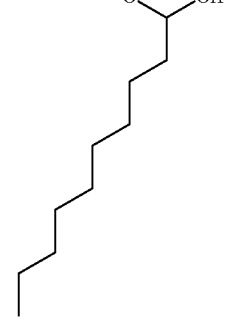

Peroxyhemiacetal made from          Peroxyhemiacetal made from
Lin-7-HP & Octanal                  Lin-7-HP & Decanal -continued

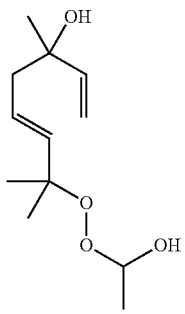

Peroxyhemiacetal made from
Lin-7-HP & Acetaldehyde

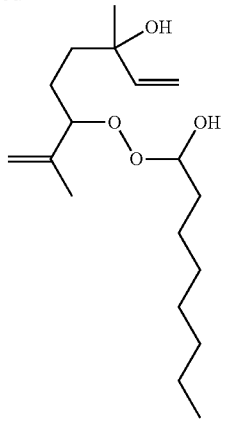

Peroxyhemiacetal made from
Lin-6-HP & Octanal

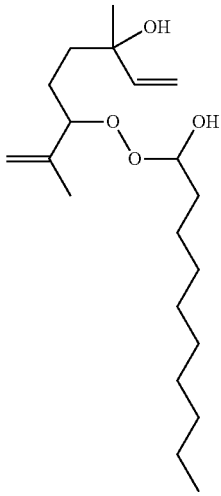

Peroxyhemiacetal made from
Lin-6-HP & Decanal

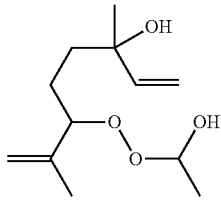

Peroxyhemiacetal made from
Lin-6-HP & Acetaldehyde

Compounds provided herein may be used for example, but not limited to laundry detergents, fabric softeners, and hard surface cleaners. In another embodiment provided herein are compounds for use in flavors for example but not limited to beverages, powdered beverages and confectionery to provide for example freshness and/or juiciness.

Preparation and Methods

The compounds claimed herein can be made using the following procedure:

Preparation of Aldehyde Stock Solutions

Approximately 400 mg of neat aldehyde (either octanal, decanal, or acetaldehyde separately) was weighed into a 5 mL volumetric flask, and diluted to volume with purified limonene, heptane, or other non-polar solvent to make an approximately 80 mg/mL stock solution.

Preparation of Terpene Hydroperoxide Stock Solutions

Approximately 5 mg of each terpene hydroperoxide (Lim-1-HP, Lim-2-HP, Lin-6-HP, or Lin-7-HP) was weighed out into separate vials, and 1.0 mL of isopropanol or ethanol was added to each, to make a series of 5 mg/mL stock solutions.

Preparation of the Peroxyhemiacetals

The reaction was set-up with a large molar excess of aldehyde present. For each possible combination of one aldehyde (octanal, decanal, or acetaldehyde) with one terpene hydroperoxide (Lim-1-HP, Lim-2-HP, Lin-6-HP, or Lin-7-HP), the procedure below was done to prepare in situ all of the possible peroxyhemiacetals that could arise from these starting compounds.

Into a 1 mL glass vial with cap was placed 0.3 mL of aldehyde stock solution and 0.1 mL of terpene hydroperoxide stock solution. The mixture was vortexed briefly, and the capped vial was allowed to stand at room temperature overnight.

Attempts at further isolation and purification cannot be performed because the formation reaction is a reversible equilibrium, so the compounds are used "as is" in a solvent appropriate for the specific usage. For example in a flavor use, limonene and ethanol would be used to prepare the respective aldehyde and hydroperoxide stock solutions.

HPLC Analysis of terpene hydroperoxides and peroxyhemiacetals was performed as described in the published method of Calandra et al, *Flavour and Fragrance Journal*, 2015, 30, 121-130.

Headspace GC/MS Analysis:

The appearance of octanal by dissociation of a peroxyhemiacetal was monitored as follows.

Gc-Ms Conditions:

Instrument: Agilent-GC-7890A, MS-7000B.

GC column: StabilWax®, containing a polyethylene glycol phase, with an inner diameter of 0.25 mm, a length of 30 m and a film thickness of 0.25 μm.

The injector temperature: 250° C.

1 μl sample is injected at constant flow (1.2 mL/min, carrier gas: helium).

MS: scan m/e 29-350

The temperature program: 40° C. (2 min) to 120° C. @ 20° C./min to 240° C. (3 min) @ 30° C./min. in a 10:1 split mode

SPME:

SPME fiber: 100 um PDMS, 23 GA, dissociated at 250° C. for 2 minutes. Between uses, the fiber was cleaned by baking for 5 min at 250° C.

Samples were placed in a 20 mL SPME vial and kept in a 25° C. thermostated block. After placement in the block, we waited for 20 minutes to allow for equilibration prior to the initial sampling. Subsequent samplings took place after another 0.33, 0.66, 1, 1.5, 2.5, 4, 24, 30, and 48 hours.

Fiber collection time: 0.5 min.

The following Examples are illustrative only and are not meant to limit the scope of the claims, the Summary, or any invention presented herein.

EXAMPLES

Example 1

Figure 2:
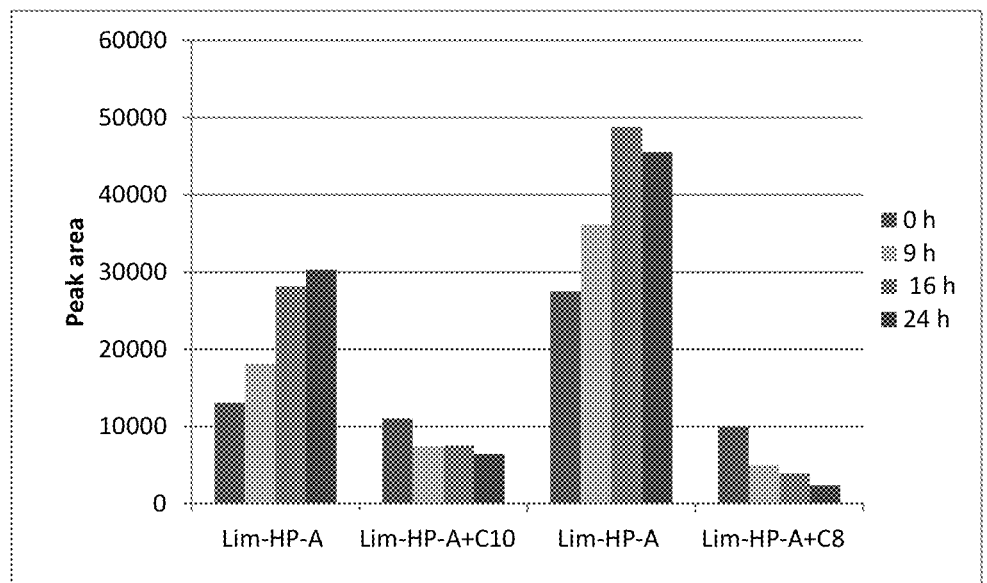
FIG. 2 shows similar release but using a difference limonene hydroperoxide isomer.
Figure 3:
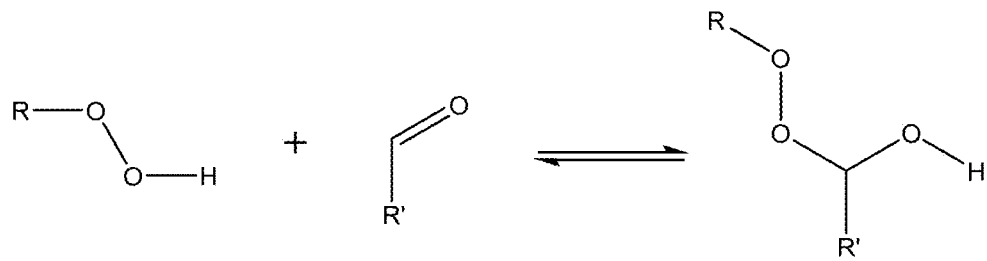
FIG. 3 shows the reversible equilibrium reaction by which the claimed peroxyhemiacetals can be made in non-polar media, and how the claimed peroxyhemiacetals can dissociate to release an aldehyde in polar or aqueous media.

Solutions of limonene hydroperoxide isomers (lim-HP-B & lim-HP-A) were separately reacted as described in Appendix 1 with decanal (C10) and octanal (C8) respectively. Note: Lim-HP-B is the 1-position isomer, and Lim-HP-A is the 2-position isomer. These products were analyzed by HPLC as described in Appendix 2. The peaks of lim-HP-B, lim-HP-A and the four peroxyhemiacetal adducts (lim-HP-B+C10, lim-HP-B+C8, lim-HP-A+C10 and lim-HP-A+C8) were monitored throughout a 24 hour period while allowed to stand on the benchtop diluted in the water/isopropanol sample preparation solvent. The peak areas of lim-HP-B and lim-HP-A increased, while the peaks of lim-HP-B+C10, lim-HP-B+C8, lim-HP-A+C10 and lim-HP-A+C8 decreased because they dissociated back to the corresponding lim-HP-B & lim-HP-A, releasing decanal or octanal respectively in the process. Results are presented in FIGS. 1 and 2.

Example 2

The peroxyhemiacetal derived from octanal and mixed isomers of limonene hydroperoxide was prepared as follows: 1.0 mL of a 117.9 mg/mL solution of limonene hydroperoxide mixed isomers in limonene solvent was placed in a 10 mL glass vial. Approximately one molar equivalent of octanal (89.7 mg) was added, and the vial was sealed then vortexed for 10 seconds. The vial was stored overnight on the benchtop (room temperature) to allow formation of the peroxyhemiacetal, then stored at −20° C. for future use.

Figure 4:
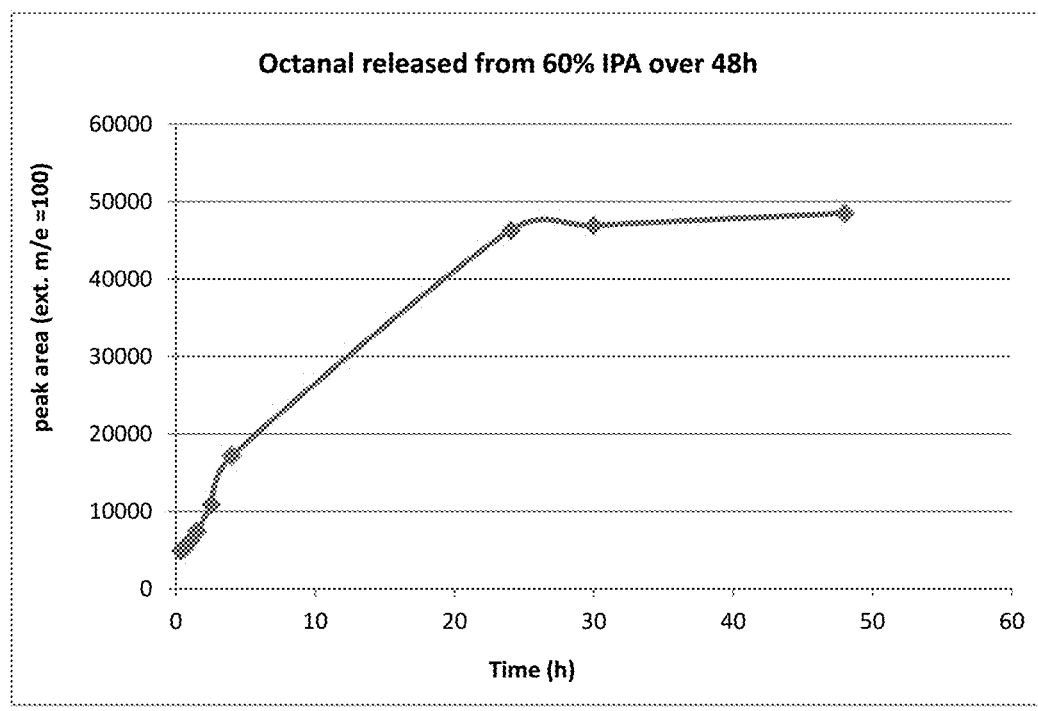
FIG. 4 shows the release of octanal from a peroxyhemiacetal dissolved in a 60/40 v/v isopropanol/water solution over 48 hours, as measured by headspace gas chromatography-mass spectroscopy.

20 microliters of the product solution prepared above was diluted with 2.0 mL of 60/40 v/v isopropyl alcohol/water. One mL of this solution was immediately transferred to a 20 mL headspace analysis vial, capped, and kept in a 25° C. thermostated block. The release of octanal from this peroxyhemiacetal was periodically monitored over 48 hours by headspace gas chromatography-mass spectrometry as described in the specification under preparation and methods. The results are shown in FIG. 4.

What is claimed is:

1. A method to improve, enhance or modify odoriferous properties of a perfuming composition or a perfumed article, which method comprises adding to said composition or article a composition consisting of a compound of Formula I

[Formula I structure: R-CH(R')-O-H]

wherein R represents a terpene hydroperoxyl selected from the group consisting of Limonene-2-hydroperoxyl; Lim-2-HP Limonene-1-hydroperoxyl; Lim-1-HP Linalool-7-hydroperoxyl; Lin-7-HP Linalool-6-hydroperoxide; Lin-6-HP wherein R' represents an alkyl group selected from the group consisting of $CH_3(CH_2)_8$—, $CH_3(CH_2)_6$—, and $CH_3$—; and wherein the compound of Formula I is in reversible equilibrium with a corresponding aldehyde and hydroperoxide;
a non-polar solvent; and
optionally an alcohol.

2. The method of claim 1, wherein the perfuming composition or the perfumed article is selected from the group consisting of laundry detergents, fabric softeners, and hard surface cleaners.

3. A composition consisting of:
a compound of Formula I

[Formula I structure: R-CH(R')-O-H]

wherein R represents a terpene hydroperoxyl selected from the group consisting of Limonene-2-hydroperoxyl; Lim-2-HP Limonene-1-hydroperoxyl; Lim-1-HP

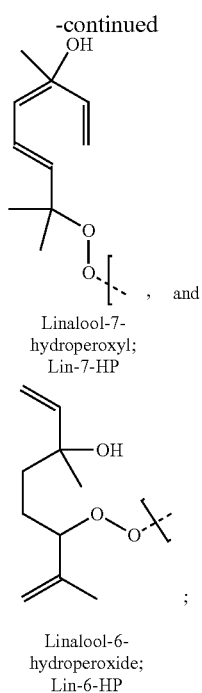

Linalool-7-hydroperoxyl; Lin-7-HP

Linalool-6-hydroperoxide; Lin-6-HP wherein R' represents an alkyl group selected from the group consisting of $CH_3(CH_2)_8-$, $CH_3(CH_2)_6-$, and $CH_3-$, and a corresponding aldehyde and hydroperoxide; and wherein the compound of Formula I is in reversible equilibrium with the corresponding aldehyde and hydroperoxide;

a non-polar solvent; and optionally an alcohol.

4. A method of delivering a compound selected from the group consisting of decanal, octanal and acetaldehyde comprising adding to an aqueous solution the composition of claim 3.

5. A composition comprising the composition of claim 3 and an aqueous solution.

* * * * *